(12) United States Patent
Aldred

(10) Patent No.: US 7,375,139 B2
(45) Date of Patent: May 20, 2008

(54) TRANSDERMAL METHOD AND APPARATUS

(76) Inventor: Katherine M. Aldred, 51 Birch St., Saugus, MA (US) 01960

( * ) Notice: Subject to any disclaimer, the term of this patent is extended or adjusted under 35 U.S.C. 154(b) by 554 days.

(21) Appl. No.: 10/642,858

(22) Filed: Aug. 18, 2003

(65) Prior Publication Data

US 2005/0042270 A1  Feb. 24, 2005

(51) Int. Cl.
*A61F 13/00*  (2006.01)
*A61K 33/26*  (2006.01)
(52) U.S. Cl. ............... 514/814; 424/449; 424/646; 424/648
(58) Field of Classification Search ............... 424/489, 424/600, 669, 709, 449, 646, 648; 514/814
See application file for complete search history.

(56) References Cited

U.S. PATENT DOCUMENTS 4,286,592 A * 9/1981 Chandrasekaran .......... 424/448
5,948,101 A * 9/1999 David et al. ................... 713/2

* cited by examiner

*Primary Examiner*—Johann R. Richter
(74) *Attorney, Agent, or Firm*—George Kessey

(57) ABSTRACT

A transdermal patch for the treatment of iron deficiency including a drug reservoir layer containing an hematinic substance; a rate-controlling membrane secured to said reservoir layer; and a contact adhesive secured to said rate-controlling membrane, wherein said hematinic substance is selected from the class consisting of ferrous sulfate, ferrous lactate, ferrous iodide, ferrous gluconate, ferrous fumarate, ferrous citrate, ferrous carbonate saccharated, ferrous carbonate mass, ferronascin, ferroglycine sulfate, and ferrocholinate.

10 Claims, 4 Drawing Sheets

TRANSDERMAL METHOD AND APPARATUS

BACKGROUND OF THE INVENTION

This invention relates to the continuous release of medication to an area of intact skin, and more particularly to the continuous release of medication to correct iron deficiency.

Various preparations are available for the treatment of anemia in patients. A typical product provides for the oral administration of iron elementals, such as ferrous fumarate. This product is available in the form of a capsule that illustratively contains about 100 mg of the iron elemental. Unfortunately, iron in therapeutic doses can produce gastrointestinal reactions, such as diarrhea or constipation. In some cases, skin rash suggesting allergy can follow the oral administration of the iron elemental. In addition, overdosage can produce iron intoxication accompanied by pallor and cyanosis, vomiting, hematemesis, diarrhea, melena, shock, drowsiness, and coma.

Other forms of iron deficiency medication can be in liquid form, but this substance can also have the same adverse effects as treatment in therapeutic doses by the use of capsules.

Accordingly, it is an object of the invention to relieve many of the contra-indications that accompany the therapeutic treatment for iron deficiency by the use of liquid elixirs and capsules.

SUMMARY OF THE INVENTION

In accomplishing the foregoing and related objects, the invention provides a transdermal patch for the treatment of iron deficiency including a drug reservoir layer; a rate-controlling membrane secured to the reservoir layer; and a contact adhesive secured to the rate-controlling membrane, wherein the reservoir contains an hematinic substance.

In accordance with one aspect of the invention, the hematinic substance is selected from the class consisting of ferrous sulfate, ferrous lactate, ferrous iodide, ferrous gluconate, ferrous fumarate, ferrous citrate, ferrous carbonate saccharated, ferrous carbonate mass, ferronascin, ferroglycine sulfate, and ferrocohnate.

In accordance with another aspect of the invention, the transdermal patch includes a protective peel strip on the contact adhesive. The transdermal patch can further include a backing layer upon the drug reservoir layer. The transdermal patch can also include a hematinic substance in the contact adhesive.

In accordance with a further aspect of the invention, the transdermal patch can have a backing layer is aluminized polyester film. The drug reservoir can include mineral oil and polyisobutylene. A contact adhesive can include mineral oil and polyisobutylene. The protective peel strip can be of siliconized polyester. When the transdermal patch is a film with a plurality of layers, they can range in thickness from 0.1 mm to 0.3 mm.

In a method of the invention for treating an iron deficiency, the steps include (a) providing a drug reservoir layer containing an hematinic substance; and (b) securing the drug reservoir layer to a skin surface. The method can further include the step of applying a rate-controlling membrane to the reservoir layer. The method can also include the step of applying a contact adhesive to the rate-controlling membrane.

The method further includes the step of selecting the hematinic substance from the class consisting of ferrous sulfate, ferrous lactate, ferrous iodide, ferrous gluconate, ferrous funarate, ferrous citrate, ferrous carbonate saccharated, ferrous carbonate mass, ferronascin, ferroglycine sulfate, and ferrocholinate. A protective peel strip can be placed on the contact adhesive, and a backing layer can be placed upon the drug reservoir layer.

The hematinic substance can be in the contact adhesive, and the backing layer can be an aluminized polyester film. The drug reservoir can be provided with mineral oil and polyisobutylene.

In a method of the invention for manufacturing a transdermal patch, the steps include; (a) providing a drug reservoir layer containing an hematinic substance; and (b) applying the layer to a rate-controlling membrane.

BRIEF DESCRIPTION OF DRAWINGS

Various other features, advantages and characteristics of the invention will become apparent after considering several illustrative embodiments, taken in conjunction with the drawings, in which.

DETAILED DESCRIPTION

Figure 1A:
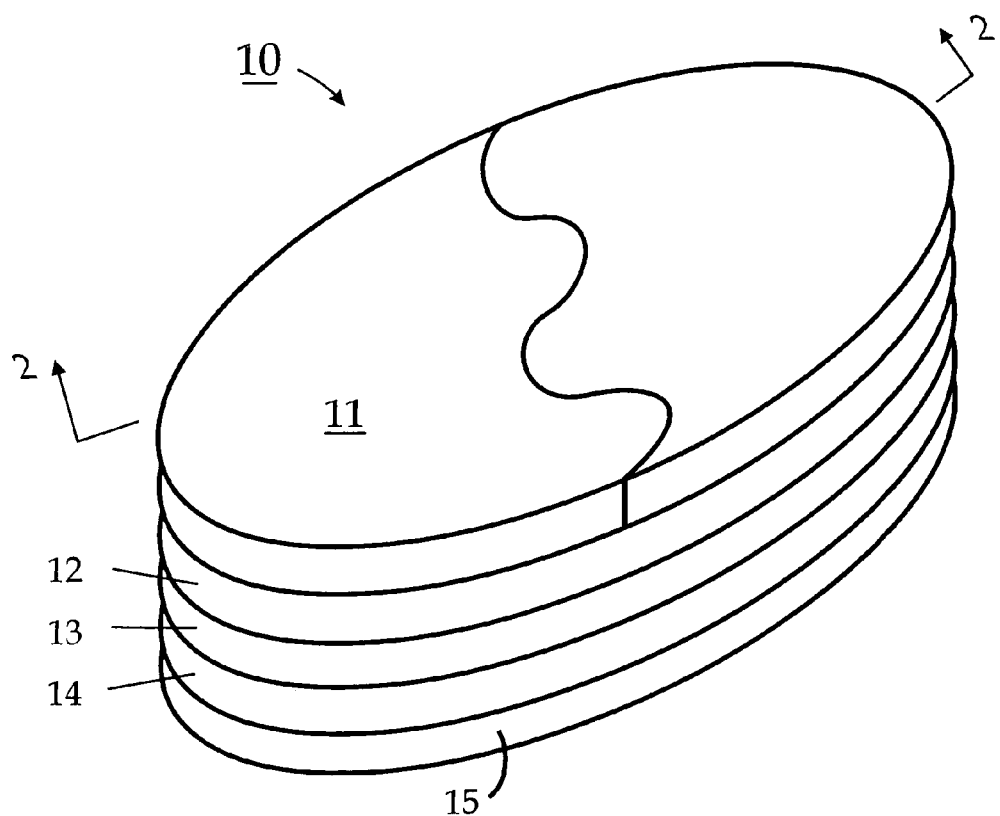
FIG. 1A is a perspective view of a transdermal patch in accordance with the invention.

With reference to the drawings, the transdermal patch 10 in accordance with the invention, is illustratively formed with a plurality of layers including a protective peel strip 11 overlying a contact adhesive layer 12, which is positioned against a rate controlling membrane 13 for a drug reservoir layer 14 upon a backing layer 15.

Figure 1B:
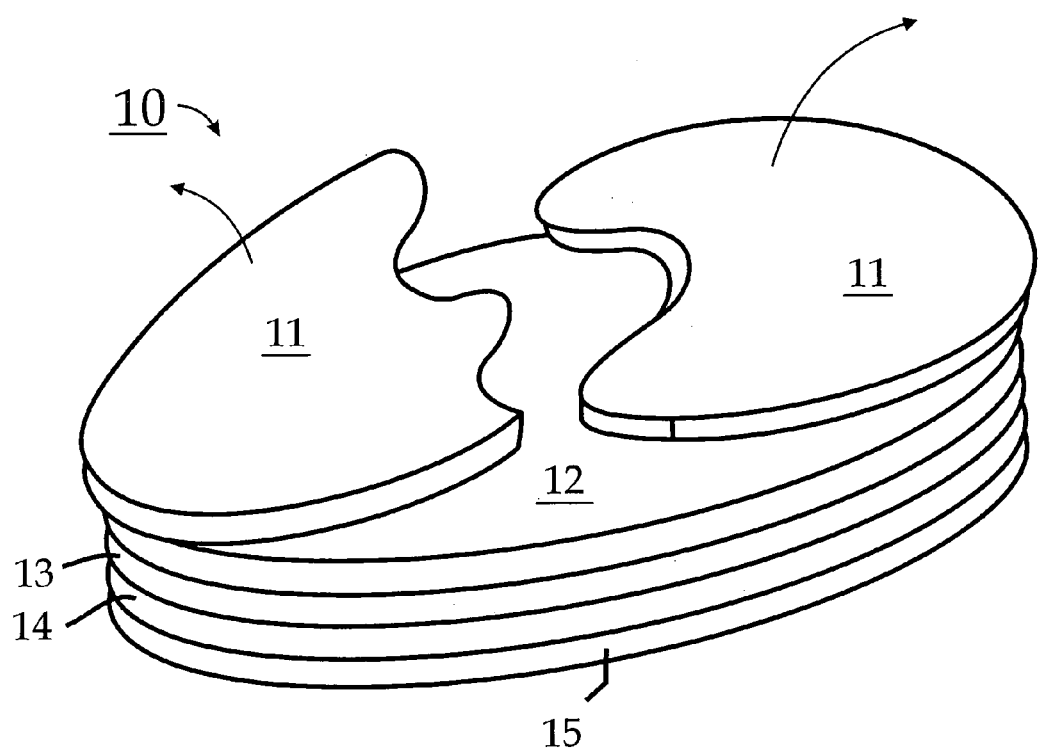
FIG. 1B illustrates the removal of the protective peel strip of the transdermal patch of FIG. 1A, prior to application to an area of intact skin.

The protective peel strip 11, which can be a siliconized polyester, is removed in accordance with FIG. 1B, prior to application of the remainder of the transdermal patch 10 of FIG. 1A, to an area of intact skin.

Figure 1C:
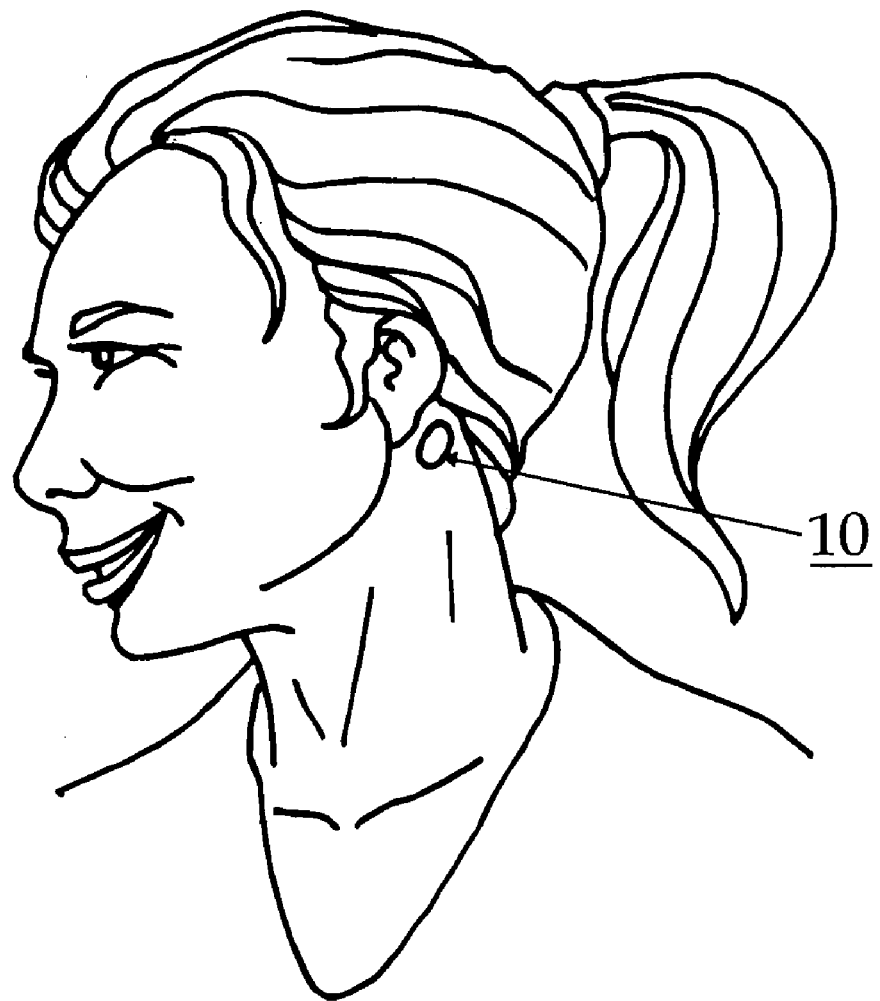
FIG. 1C illustrates application of the transdermal patch of FIG. 1B after removal of the protective peel strip to an area of intact skin on the head, behind the ear.
Figure 2:
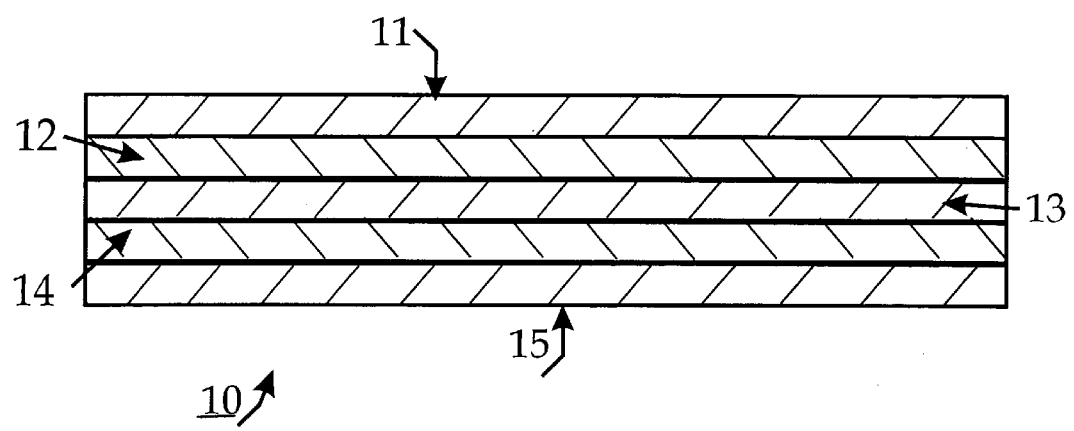
FIG. 2 is a cross-section of the transdermal patch of FIG. 1A.

As illustrated in FIG. 1C, the transdermal patch 10 of FIG. 1B can be applied to an area of intact skin on the head, behind the ear. It will be understood that the transdermal patch 10 may be applied to intact skin in any area of the body. The area behind the ear is desirable because the patch is relatively inconspicuous and not easily disturbed, being protected by the ear as a shield The various layers of the patch 10 are shown in cross-section in FIG. 2. It will be appreciated that, although the patch 10 is ellipsoidal, other configurations may be used as well, such as circular, rectangular, etc. In addition, the protective peel strip is provided with an intermediate undulated edge to facilitate removal. Other forms of peel edge may be used instead.

The patch 10 contains a suitable amount of hematinic in the drug reservoir layer 14, ranging from about 0.1 to about 2.0 milligrams. The amount of hematinic included in the drug reservoir layer 14 depends upon the treatment regimen. The rate-controlling membrane is microporous to control the rate of delivery from the patch to the skin surface and is programmed to deliver between about 0.03 to about 0.7 milligrams at an approximately constant rate to the systemic circulation over the lifetime of the patch 10, which can range from about 2 days to 10 days.

An initial priming dose of hematinic can be released from the adhesive layer 12 of the patch 10 to saturate skin binding sites and rapidly bring the concentration of the hematinic to a required steady-state level. Thereafter, a continuous controlled release of hematinic flows from the drug reservoir 14 through the rate-controlling membrane 13 to maintain the release level constant.

The sole active ingredient of the patch 10 is the hematinic, which can be selected from among various substances such as ferrous sulfate, ferrous lactate, ferrous iodide, ferrous gluconate, ferrous fumarate, ferrous citrate, ferrous carbonate saccharated, ferrous carbonate mass, ferronascin, ferroglycine sulfate, and ferrocholinate.

Ferrous sulfate illustratively has a molecular weight of 151.91 and is approximately 37% iron, 42% oxygen, and 21%. Hydrates occur in mineral form including the monohydrate which is a white to yellow crystalline powder that loses moisture at about 300° C. The heptahydrate, which is prepared commercially by the action of sulfuric acid on iron, is a blue-green monoclinic crystal which effloresces in dry air and oxidizes in moist air to form a coating of basic ferrous sulfate. Ferrous sulfate is soluble in water and oxidizes slowly in air when cold, rapidly when hot and is a suitable therapeutic for iron deficiencies.

Alternatively, the transdermal delivery system for delivering a hematinic to the blood can include a vasodilator, the hematinic, a permeation enhancer for the hematinic, and a water-soluble gum binder. To control the microenvironment at the transport site on intact skin, a non-breathable layer can be used In addition, compression can be used to enhance the blood supply at the transport site.

A transdermal drug delivery system permits localized delivery of drug molecules so that the drug delivery is target-specific, and avoids gastrointestinal complications that often accompany oral delivery. Transdermal drug delivery desirably employs patch technology, which is based on the ability of the patch to hold an active ingredient in constant contact with the skin. Over time, drug molecules, held in the patch, will reach the bloodstream.

In order for the hematinic to reach the bloodstream, it must pass through a dense layer of cells, known as the stratum corneum, the dermis, and the capillary cell structure. Although patch adhesion to the skin can cause skin trauma, as well as cosmetic problems, it is desirable to choose an inconspicuous area of the skin for patch application.

In order to enhance the delivery of the hematinic, penetration enhancers can be added, such as menthol, vegetable oil or eucalyptol. The molecular delivery system can contains, beside the active drug molecule, an ensemble of four elements, including, a vasodilator, a penetration enhancer, and a water soluble gum for linking the vasodilator, the penetration enhancer and active hematinic.

The vasodilator enhances blood flow to the transport site. Regardless of metabolism, obesity or circulatory efficiency, the vasodilator increases blood flow to the transport site to reliably enhance absorption of the hematinic molecule. Where transport speed of the hematinic is sufficient, a patch can be eliminated.

The vasodilator expands the blood supply to and from the local vascular network as well as to the subdermal layer. Suitable ratios of vasodilators range from about 1% to about 80% by weight, with ratios of from about 1% to about 33% being preferred The amount of vasodilator will vary due to a number of factors, including the drug molecule size, drug concentration, the desired delivery speed, the size of the surface area of an application, and the application site.

Excess amounts of vasodilators can be used without impacting performance. Examples of non-irritational vasodilators include, bamethan sulphate, bencyclane fumarate, benpurodil hemisuccinate, benzyl nicotinate, buflomedil hydrochloride, buphenine hydrochloride, butalamine hydrochloride, cetledil citrate, ciclonicate, cinepazide maleate, cyclandelate, di-isopropylammonium dichloroacetate, ethyl nicotinate, hepronicate, hexyl nicotinate, Ifenprodil tartrate, inositol nicotinate, isoxsuprine hydrochloride, kallidinogenase, methyl nicotinate, maftidropuryl oxalate, nicametate citrate, niceritrol, nicobuxil, nicofuranose, nicotinyl alcohol, nicotinyl alcohol tartrate, nonidamide, oxpentifylline, papaveroline, pentifylline, pipratecol, propentofylline, raubasine, suloctidil, teasuprine, thymoxamine hydrochloride, xanthinol nicotinate, diazoxide, hydralazine, minoxidil and sodium nitropusside. Centrally acting agents include clonidine, quanaberz and methyl dopa. Alpha-adrenocaptor agents include indoramin, phenoxybenzamine, phentolamine and prazosin. Adrenergic neuron blocking agents include bethanidine, debrisoquine and guanethidine. ACE inhibitors include benazepril, captopril, cilazapril, enalapril, fosinopril, lisinopril, perindopril, quinapril and ramipril. Ganglion-blocking agents include pentolinium and trimetaphan. Calcium-channel blockers include amlodipine, diltiazem, felodipine, isradipine, nicardipine, nifedipine, nimodipine and verapamil. Prosteglandins include prostacyclin, thrombuxane $A_2$, leukotrienes, PGA, $PGA_1$, $PGA_2$, $PGE_1$, $PGE_2$, PGD, PGG and PGH. Angiotension II analogs include saralasin. Other vasodilators include nitroglycerin, labetalol, thrazide, isosorbide dinitrate, pentaerythritol tetranitrate, digitalis, hydralazine, diazoxide and sodium nitroprusside. One or more vasodilators can be used.

Suitable penetration enhancers include vegetable oil or a vegetable oil/alcohol mix. Suitable vegetable oils include peanut oil, olive oil, sunflower oil, soybean oil, monoi oil and macadamia oil, with olive oil being preferred Suitable alcohols for the vegetable oil/alcohol mix include ethyl alcohol, isopropyl alcohol, methanol and witch hazel. Olive oil mixed with isopropyl alcohol is a preferred vegetable oil/alcohol mix. Eucalyptol is a further suitable example of a vegetable oil/alcohol mix. Suitable ratios of vegetable oil:alcohol range from about 5:1 to about 1:10, preferably 1:2. Suitable amounts of vegetable oil or vegetable oil/alcohol mix range from about 1% to about 66% by weight, more preferably from about 10% to about 33.3% by weight.

The penetration enhancer, the vasodilator, and the hematinic are placed in a mixing vessel, and the combination agitated achieve a uniform mix. Other inactive ingredients may be added if desired.

It will be appreciated that the foregoing embodiments are merely illustrative and that other variations in form and substance may be made without departing from the spirit and scope of the invention as defined in the appended claims.

I claim:

1. A method of treating iron deficiency in a patient in need thereof comprising the steps of:
   (a) providing a drug reservoir layer containing an hematinic substance; and
   (b) securing said drug reservoir layer to a skin surface.

2. The method as defined in claim 1, further including the step of applying a rate-controlling membrane to said reservoir layer.

3. The method as defined in claim 1, further including the step of applying a contact adhesive to said rate-controlling membrane.

4. The method as defined in claim 1, further including the step of selecting said hematinic substance from the class consisting of ferrous sulfate, ferrous lactate, ferrous iodide, ferrous gluconate, ferrous fumarate, ferrous citrate, ferrous carbonate saccharated, ferrous carbonate mass, ferronascin, ferroglycine sulfate, and ferrocholinate.

5. The method as defined in claim 1, further including the step of including a protective peel strip on said contact adhesive.

6. The method as defined in claim 1, further including the step of including a backing layer upon said drug reservoir layer.

7. The method as defined in claim 1, further including the step of including a hematinic substance in said contact adhesive.

8. The method as defined in claim 1, further including the step of providing said backing layer as aluminized polyester film.

9. The method as defined in claim 1, further including the step of providing said drug reservoir with mineral oil and polyisobutylene.

10. The method of manufacturing a transdermal patch comprising the steps of;
   (a) providing a drug reservoir layer containing an hematinic substance; and
   (b) applying said layer to a rate-controlling membrane.

* * * * *